US00PP14421P39

(12) United States Plant Patent
Horvath

(10) Patent No.: US PP14,421 P3
(45) Date of Patent: Dec. 23, 2003

(54) *SEDUM TELEPHIUM* PLANT NAMED 'LAJOS'

(50) Latin Name: *Sedum telephium*
Varietal Denomination: Lajos

(76) Inventor: Brent Horvath, 10702 Seaman Rd., Hebron, IL (US) 60034

( * ) Notice: Subject to any disclaimer, the term of this patent is extended or adjusted under 35 U.S.C. 154(b) by 0 days.

(21) Appl. No.: 09/898,768

(22) Filed: Oct. 1, 2001

(65) Prior Publication Data

US 2003/0066113 P1 Apr. 3, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,895 P2 * 8/2002 Bergman ..... Plt./291

OTHER PUBLICATIONS

Peter Walton, Principles and Practices of Plant Science, Ed. Ellen Denning, Prentice Hall, New Jersey, 1988, pp. 29–30.*
The New Royal Horticultural Society Dictionary of Gardening, 1992. The Stocton Press, New York, pp. 244–252.*
http://www.susansgardenpatch.com/perennials5.htm, Sep. 1, 2002, pp. 1–3.*
http://www.mooseyscountrygarden.com/gallery/foliage-.html, Sep. 1, 2002, pp. 1–3.*
http://www.hcs.ohio–state.edu/hort/plantlisting/S/Sedum4275.html, Sep. 1, 2002, p. 1.*
http://www.forestfarm.com/search/closeup.asp?PlantID=seka015, Sep. 1, 2002, pp. 1–2.*
http://www.chicagolandgardening.com/CGMPages/qanda.htm, Sep. 1, 2002, pp. 1–7.*

* cited by examiner

*Primary Examiner*—Anne Marie Grunberg
(74) *Attorney, Agent, or Firm*—Brent Horvath

(57) ABSTRACT

A new, distinct *Sedum telephium* characterized by a creamy yellow margin to the foliage.

2 Drawing Sheets

Latin name: *Sedum telephium.*
Cultivar name: 'Lajos'.

BACKGROUND OF THE INVENTION

The present invention relates to a new form of *Sedum telephium* plant named 'Lajos', pronounced "Lai'-osh". A naturally occurring sport or mutation of *Sedum telephium* 'Autumn Joy' characterized by a butter yellow edge to the foliage, compared to the all green leaves of *Sedum telephium* 'Autumn Joy'. The parent plant, *Sedum telephium* 'Autumn Joy' is of hybrid origin between *Sedum telephium* and *Sedum spectabile*. The new plant was found as a single 1 gallon plant by the inventor among a block of 1 gallon *Sedum telephium* 'Autumn Joy' at a wholesale perennial nursery in Harvard, Ill. in 1997. The selection of this plant was due to it's variegated foliage. Asexual, vegetative tip cutting propagation and division has been the only means of reproduction. Propagation has taken place at Intrinsic Perennial Gardens, Inc. Hebron, Ill. since 1998. In 1999 we planted four plants out in three different locations. To date these four plants have not had any reverting. The new Sedum has shown to be stable and identical in reproduction to the parent after rooting over 500 vegetative tip cuttings from 1998 to 2002.

SUMMARY OF THE INVENTION

In the following description, color references are made to The Royal Horticultural Society Colour Chart. The new *Sedum telephium* plant named 'Lajos' has shown the characteristic of a yellow variegation on a tall upright Sedum to be unique and stable. Plants of the new Sedum can be compared to plants of *Sedum alboroseum* 'Frosty Morn'. 1. The new Sedum is a sport occurring on a hybrid with

*telephium* while the 'Frosty Morn' species is *alboroseum.* 2. The new Sedum has a yellow variegation, yellow group 11 C, while 'Frosty Morn' has a white variegation. 3. The new Sedum has a broader variegation, typically a 5 mm wide edge to the leaf while 'Frosty Morn' has a thinner variegation, typically 2–3 mm wide.

Plants of the new Sedum can also be compared to plants of *Sedum kamtchaticum* 'Variegatum'. 1. The new Sedum is typically upright on strong stems 30–45 cm tall while *Sedum kamtchaticum* 'Variegatum' is typically 10 cm high. 2. The leaf size of the new Sedum is larger as well, usually 5–8 cm long and 3–4 cm wide, while *Sedum kamtchaticum* 'Variegatum' leaves are usually 10–15 mm long and 10 mm wide. 3. The new Sedum has an overall flower color of 187 D while *Sedum kamtchaticum* 'Variegatum' has yellow or gold flowers.

DESCRIPTION OF PHOTOGRAPHS

1. Top view of the first sheet is of a growing tip.
2. Bottom view of the first sheet is a close up of variegated foliage.
3. Top view of the second sheet is of the new Sedum plant in bud in July.
4. Top view of the second sheet is a close up of flowering with the variegated foliage.

DETAILED BOTANICAL DESCRIPTION

In the following description, color references are made to The Royal Horticultural Society Colour Chart.

Botanical classification: *Sedum telephium* cultivar 'Lajos'.
Parentage: *Sedum telephium* 'Autumn Joy'.
Propagation: Vegetative tip cuttings and division.
Plant description: Overall habit of the new Sedum is strongly clumping mounds with upright stems topped by reddish purple flowers in September. Vigor is moderate.

*Plant height.*—30–45 cm.
*Plant width.*—30–45 cm.
*Stem diameter.*—5–12 mm.

Foliage:

*Type.*—Deciduous.
*Shape.*—Obovate.
*Petiole.*—None.
*Length.*—5–8 cm.
*Width.*—3–4 cm.
*Thickness.*—1–2 mm.
*Margin.*—Coarsely and irregularly toothed.
*Texture.*—Smooth.
*Leaf arrangement.*—Alternate, crowded except at the base of the stems.
*Leaf pattern.*—The typical measurements of the leaf patterns are 2–3 cm wide and 4–7 cm long green centers with typically 5 mm of variegation along the entire edge.
*Adaxial leaf description.*—The variegated edge is yellow color 11 C. The center of the adaxial side of the leaf is green color 137 A.
*Abaxial leaf description.*—The variegated edge is yellow color 11 C. The center of the abaxial side of the leaf is green color N138 C.

Flower:

*Petal count.*—5.
*Flower type.*—Panicle.
*Panicle color.*—As a whole the color is 187 D.
*Flower size.*—3 mm across, 5 mm tall.
*Carpel color.*—61 A.
*Sepal size.*—1 mm across, 2 mm tall.
*Sepal color.*—11 C.
*Peduncle color.*—145 B.
*Flower number.*—Approximately 2000–3000 per mature panicle measuring 10–15 cm.
*Fertility.*—Sterile, no anthers, no stamens.
*Blooming habit.*—Domed, terminal panicle on up to 45 cm stems.
*Bloom period and duration.*—September into October.
*Scent.*—No scent noticed.
*Bud color.*—158 B.
*Bloom color.*—187 D.
*Fruit.*—None.
*Disease resistance.*—Resistance to diseases common to Sedum has not been observed on plants grown under nursery conditions.

I claim:

1. A new, distinct *Sedum telephium* plant as shown and described, characterized by a creamy yellow edge to the foliage.

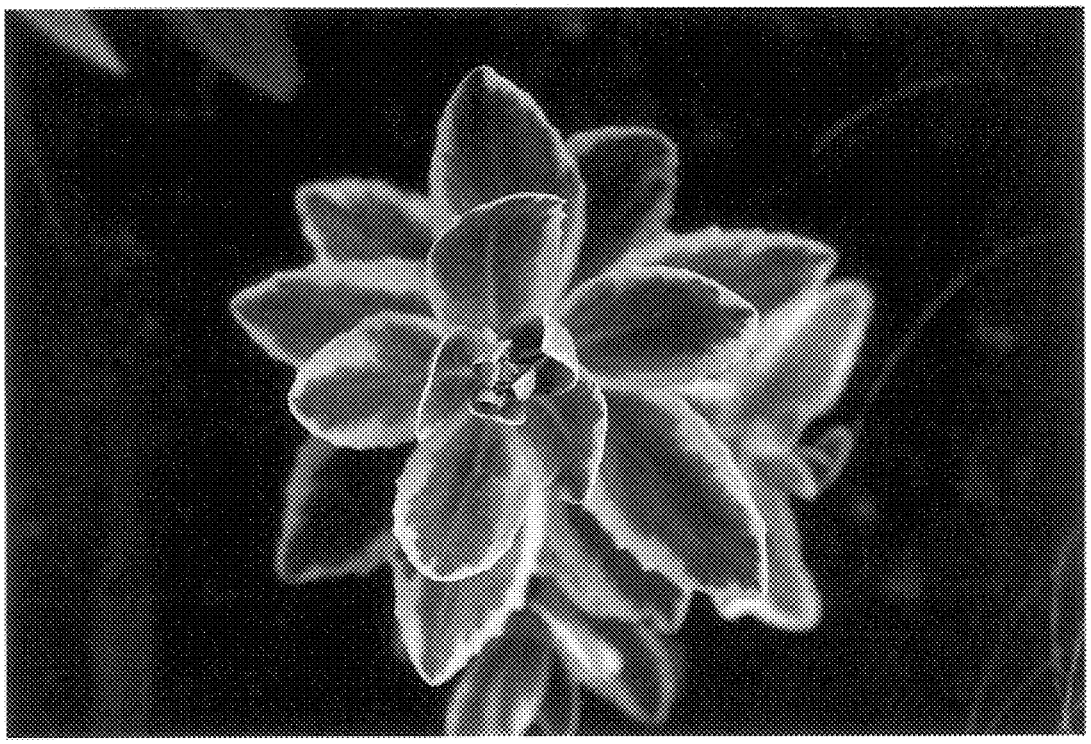
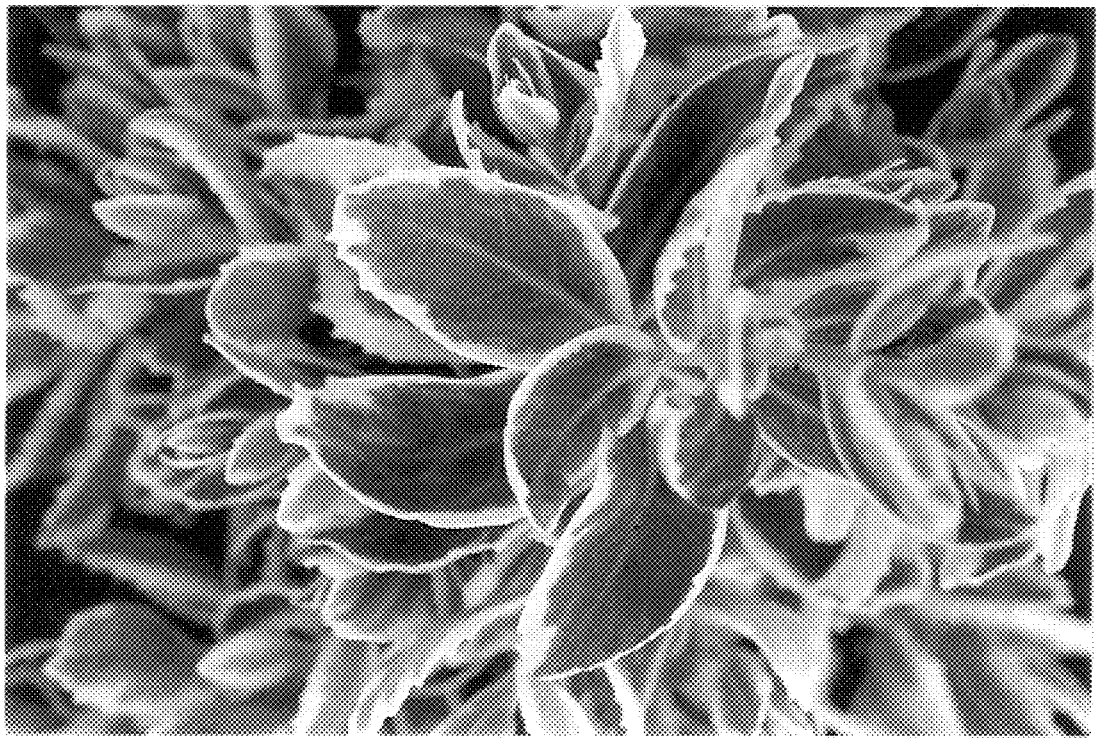

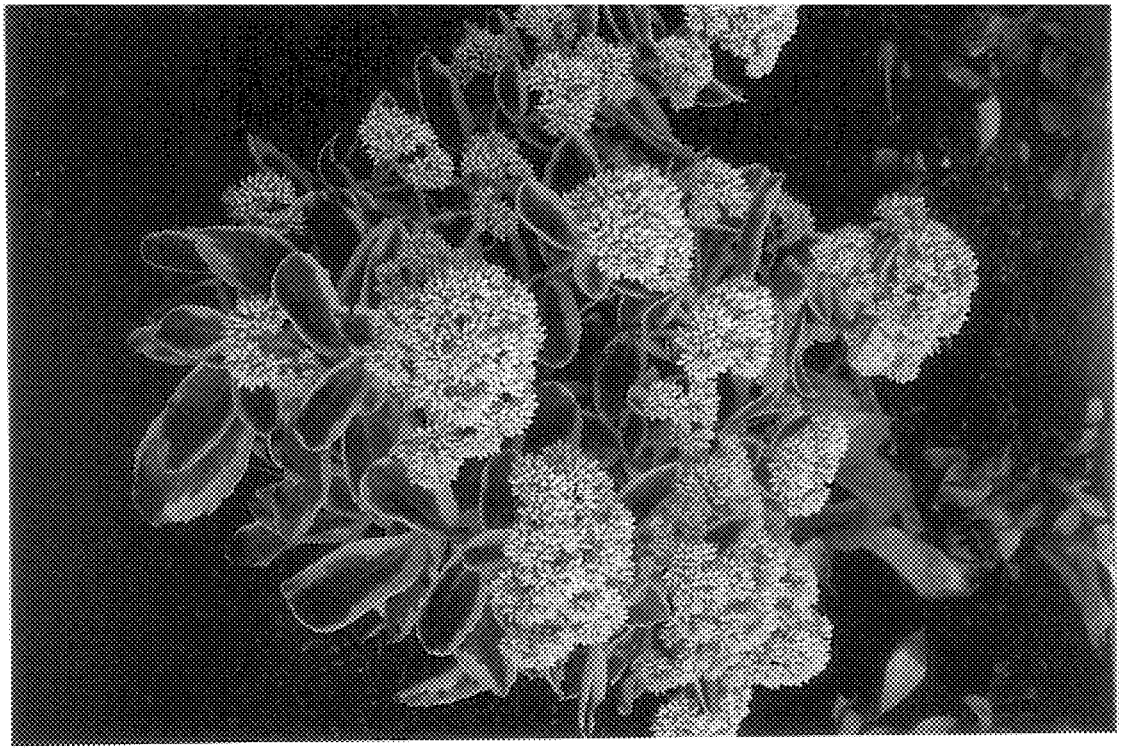
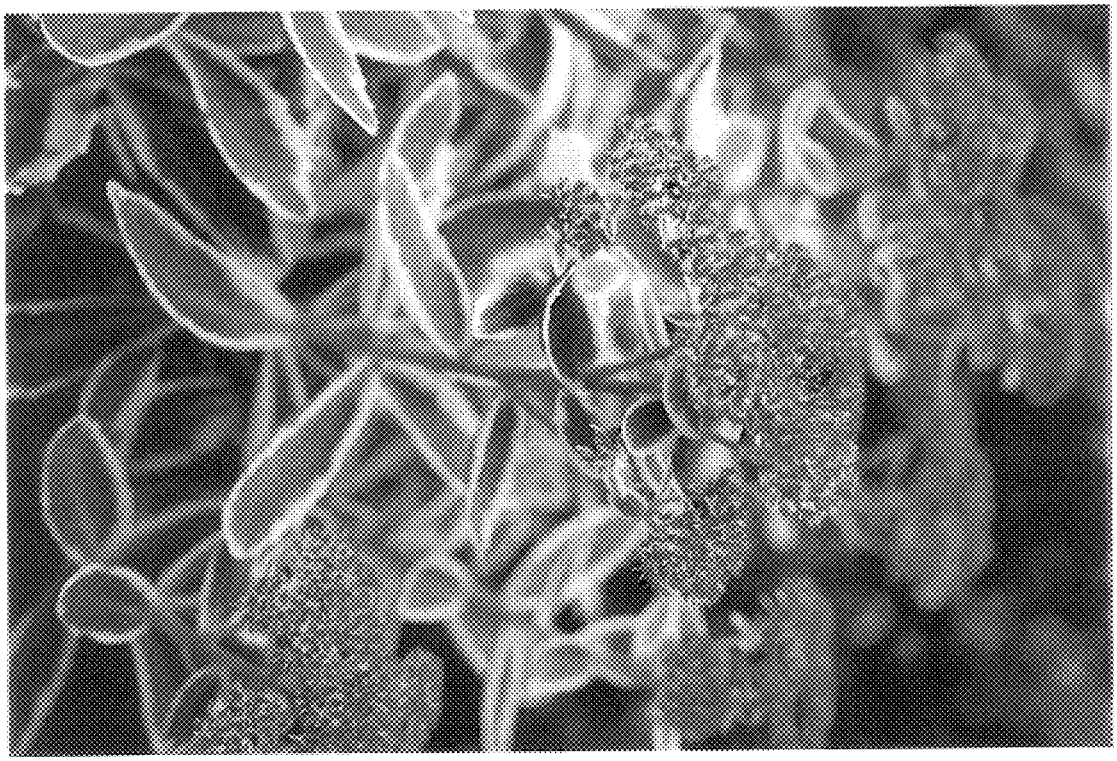

* * * * *